United States Patent [19]

Goze et al.

[11] Patent Number: 5,015,415
[45] Date of Patent: May 14, 1991

[54] N,N-DISUBSTITUTED PHTHALAMIC ACIDS AND THEIR AMMONIUM SALTS, AND THEIR USES THEREOF AS SURFACTANTS, EMULSIFIERS, AND CONDITIONING AGENTS IN SHAMPOOS

[76] Inventors: Jean M. Goze, 757 NE. Holcomb Dr., Mundelein, Ill. 60060; Randal J. Bernhardt, 1905 E. Fairfield Rd., Lindenhurst, Ill. 60046; Branko Sajic, 5048 N. Ridgeway Ave., Chicago, Ill. 60625; Ned M. Rockwell, 301 Neuman Ct., Lake Bluff, Ill. 60044; Nina M. McConnell, 894 Burr Ave., Winnetka, Ill. 60093; William R. Mohring, 4400 Lake Ave., Apt. 109A, Glenview, Ill. 60025

[21] Appl. No.: 542,780

[22] Filed: Jun. 27, 1990

[51] Int. Cl.$^5$ .................... C11D 1/62; C11D 3/30; A61K 7/075
[52] U.S. Cl. .................... 252/547; 252/546; 252/527; 252/528; 252/DIG. 13; 252/174.15; 424/70
[58] Field of Search .............. 252/547, DIG. 13, 546, 252/527, 528, 174.15; 424/70

[56] References Cited
U.S. PATENT DOCUMENTS

| | | | |
|---|---|---|---|
| 2,072,770 | 3/1937 | Held | 134/57 |
| 2,101,323 | 12/1937 | Salzberg | 106/186 |
| 4,117,531 | 9/1978 | Ross | 361/433 |
| 4,210,424 | 7/1980 | Feldman et al. | 44/62 |
| 4,375,973 | 3/1983 | Rossi et al. | 44/62 |
| 4,402,708 | 9/1983 | Oswald | 44/66 |

Primary Examiner—Paul Lieberman
Assistant Examiner—Erin M. Higgins

[57] ABSTRACT

The invention encompasses formulated conditioning shampoos, surfactant solutions and emulsifier solutions comprising effective amounts of salts of the following general formula

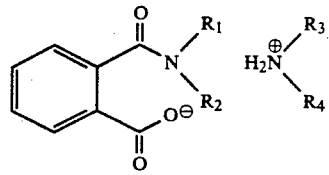

wherein
$R_1$, $R_2$, $R_3$, and $R_4$ are the same or different and represent straight or branched chain alkyl groups having 10 to 40 carbon atoms, or aryl straight or branched chain alkyl groups having 10 to 40 carbon atoms.

The invention also encompasses formulated conditioning shampoos, surfactant solutions, and emulsifier solutions comprising effective amounts of mixtures of a salt of formula I and an acid of formula II

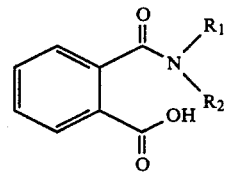

wherein
$R_1$ and $R_2$ are the same or different and represent straight or branched chain alkyl groups having 10 to 40 carbon atoms, or aryl straight or branched chain alkyl groups having 10 to 40 carbon atoms.

27 Claims, No Drawings

N,N-DISUBSTITUTED PHTHALAMIC ACIDS AND THEIR AMMONIUM SALTS, AND THEIR USES THEREOF AS SURFACTANTS, EMULSIFIERS, AND CONDITIONING AGENTS IN SHAMPOOS

BACKGROUND OF THE INVENTION

1. Field of the Invention

This invention relates to the use of N,N-disubstituted phthalamic acids and/or N,N-disubstituted phthalamic acid ammonium salts, their use as surfactants, emulsifiers and conditioning agents in shampoos.

2. Description of the Related Art

Human hair becomes soiled due to its contact with the surrounding atmosphere and, to a greater extent, from sebum secreted by the head. The build-up of the sebum causes the hair to have a dirty feel and an unattractive appearance. The soiling of the hair necessitates its being shampooed with frequent regularity.

Shampooing the hair cleans by removing excess soil and sebum. However, the shampooing process is disadvantageous because the process results in hair that is left in a wet, tangled and generally unmanageable state. A variety of approaches have been developed to alleviate the after-shampoo problems. These range from the inclusion of hair conditioning aids in shampoos to post-shampoo application of hair conditioners, i.e., hair rinses. Hair rinses typically work by depositing a polymeric film or other material onto the hair. However, the use of such solutions as conditioners has not been fully satisfactory. For one thing, hair rinses are generally liquid in nature and must be applied in a separate step following the shampooing, left on the hair for a length of time, and finally rinsed with fresh water. This, of course, is time consuming and inconvenient. Furthermore, hair rinses or the leave-on hair conditioners, in addition to requiring an extra step, are difficult to apply in just the right amount of product and are not evenly distributed throughout a head of hair.

While shampoos have been disclosed which contain conditioning aids, these shampoos have not been totally satisfactory for a variety of reasons. One reason relates to a lack of compatibility between surfactants which are good cleaning agents and fatty cationic agents which are good conditioning agents. This lack of compatibility caused other surfactants such as nonionics, amphoterics and zwitterionics to be examined by workers in the field. However no satisfactory solutions have been found. Shampoo conditioners must be applied in a separate step after shampooing, left on the hair for a period of time and then rinsed with water. This process is time consuming and inconvenient.

Suspending/emulsifying agents have been used for cationics in shampoo compositions with surfactants and silicone materials. Normally, a suspension system comprising of xanathan gum, glycerol distearate and cetyl alcohol is used. Manufacturing these compositions is extremely complex, costly and time consuming.

U.S. Pat. No. 4,741,855 describes shampoo compositions which comprise a synthetic surfactant, an insoluble, non-volatile silicone, a suspending agent, and water. The described suspending agents include long chain esters of ethylene glycol, esters of long chain fatty amine oxides and many others. There appear to be several key conditioning components in these compositions, including an insoluble, non-volatile silicone, a suspending agent and a quaternary ammonium compound. The quaternary ammonium compounds, disclosed in U.S. Pat. No. 4,741,855 as ingredients in a shampoo composition are di(hydrogenated tallow) dimethyl ammonium chloride and cetyltrimethyl ammonium chloride.

The use of silicone material in shampoos has been described in a number of different publications. The manufacture of such compositions is extremely complicated and requires specialized mixing equipment, high shear pumps, a heat exchanger, several manufacturing tanks, etc.

Quaternary ammonium compounds derived from fatty acid amines such as tallow amine and di-tallow amine have been used as conditioners, surfactants and thickeners or emulsifiers in various shampoo and hair care products. For example, European Patent Application No. 0067635A2 discloses conditioning shampoos containing quaternary ammonium compounds of the formula:

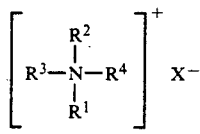

wherein the $R^1$ and $R^2$ groups contain an average of from about 16 to 22 carbon atoms most preferably from about 16 to about 18 carbon atoms, $R^3$ and $R^4$ are $C_1$ to $C_4$ alkyl or hydroxyalkyl groups, and X is any compatible anion, particularly one selected from the group consisting of halide, hydroxide, methylsulfate, or acetate anions.

The shampoo compositions of that patent application also contain acyl derivatives which are long chain amides, alkanolamides, esters of ethylene glycol and glycerine, esters of carboxylic acids. esters of thiodicarboxylic acids, and mixtures of these derivatives. The shampoo compositions of that patent application also contain surfactants which are represented by the formula:

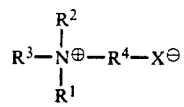

wherein $R^1$ is a long chain alkyl radical having from about 10 to about 18 carbon atoms or an amido radical represented by the formula:

$$R^5-CONH(CH_2)_3$$

wherein $R^5$ is a long chain alkyl radical, $R^2$ and $R^3$ are each alkyl radicals having from about 1 to about 3 carbon atoms. $R^4$ is an alkylene or hydroxy alkylene radical having from about 1 to about 4 carbon atoms and X is a carboxylate radical.

European Patent Application No. 0 152 194 A2 discloses shampoo compositions containing quaternary ammonium salts of the formula:
wherein $R_1$ is hydrogen, or an aliphatic group of from 1 to 22 carbon atoms, or an aromatic, aryl or alkaryl group having 6 to 20 carbon atoms; $R_2$ is an aliphatic group having from 12 to 22 carbon atoms; $R_3$ and $R_4$ are each alkyl groups having from 1 to 3 carbon atoms; and X is an anion selected from halogen, acetate, phosphate, nitrate and methyl sulfate radicals.

U.K. Patent Application No. GB 2196979 A provides hair care compositions comprising compounds of the formula:
wherein $R_1$ and $R_2$ are aliphatic groups containing from about 12 to about 22 carbon atoms, $R_3$ and $R_4$ are hydrogen or short chain alkyl groups containing from about 1 to about 4 carbon atoms and X is anion selected from halogen, acetate, phosphate, nitrate and alkyl sulfate radicals.

U.K. Patent Application No. GB 2124647 A teaches quaternary ammonium compounds useful in shampoo compositions. The ammonium compounds have the formula:

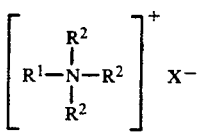

or

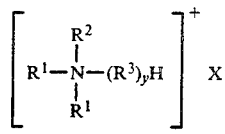

wherein $R_1$ is an aliphatic alkyl group containing an average of from about 16 to 22 carbon atoms, most preferably from about 16 to about 18 carbon atoms, the $R_2$ groups are $C_1$ to $C_4$ alkyl or hydroxylalkyl groups, the $R_3$ groups are alkylene oxide groups, preferably propylene oxide, where y is 1–4 and X is any compatible anion, particularly one selected from the group consisting of halide, hydroxide, methylsulfate, or acetate anions.

European Patent Application No. 0294 894 discloses conditioning agents for delivery from shampoos comprising compounds of the formula:

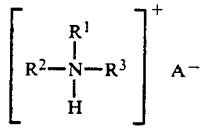

wherein $R_1$ and $R_2$ can independently be $C_{16}$ to $C_{20}$ alkyl or alkenyl and $R^3$ is H or $CH_3$, and A is an anionic surfactant selected from the group consisting of alkyl sulfonates, aryl sulfonates, alkylaryl sulfonates, alkyl sulfates, alkyl ethoxylated sulfates, dialkyl sulfosuccinates, ethoxylated alkyl sulfonates, alkyl oxybenzene sulfonates, acyl isethionates, acyl alkyl taurates, olefin sulfonates and paraffin sulfonates.

A wide variety of surface active (surfactant) compounds are known and widely used. Further, certain relatively specific phthalamate derivatives are at least nominally disclosed in academic and patent literature. Some specific phthalamate derivatives have been suggested as being useful in plant growth regulator formulations insect repellent formulations, bactericidal. fungicidal, herbicidal formulations, additives for improving low temperature flow characteristics of petroleum distillate fuels, solvent extraction formulations for certain heavy metal ions, catalyst systems for polyurethane foam formulations, additives for thermal recording materials, thickeners for silicone grease and oil-based drilling muds, additives for water-insensitive coatings, plasticizers, etc. Phthalamic acids or phthalamate derivatives have been used as additives for insecticidal compositions; additives for vulcanization activators; additives for rust and corrosion inhibitor formulations; additives to screen-clogging prevention and rust inhibition formulations; additives for improving low temperature flow characteristics of petroleum fuel oils; additives to catalyst systems for polyurethane foam formulations.

Ammonium phthalamates have been used as additives in fuel oil compositions, blending agents for grease, lubricating oil additives, and thickening agents for lubricating oil compositions. These ammonium phthalamates have the formula

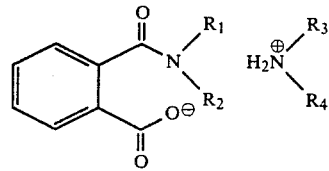

wherein
$R_1$, $R_2$, $R_3$ and $R_4$ are the $C_{16}$–$C_{40}$, preferably $C_{16}$–$C_{24}$ straight chain alkyl groups of secondary amine, and may be the same or different.

Tallow is a fatty acid byproduct of the meat-packing industry obtained by rendering the body fat from cattle and sheep. Tallows from different sources vary in free fatty acid content. The fatty acids normally found in tallow are myristic acid, palmitic acid, stearic acid, oleic acid, and linoleic acid.

Several methods are known for the preparation of tallow amines, but the most common method in industry is the conversion of a fatty acid to a nitrile by treating with ammonia, followed by catalytic hydrogenation of the nitrile to primary, secondary, or tertiary amine by suitable adjustment in the reaction conditions. Tallow amines as well as di(hydrogenated tallow) amine, are commercially available; for example, di(hydrogenated tallow) amines are available under the trade name ARMEEN 2HT ™ (Akzo Chemicals, Chicago, Ill.).

Various routes exist for the preparation of phthalamic acids and phthalamic acid salts. In U.S. Pat. No. 4,402,708 N,N-diarachidyl phthalamic acid was prepared by adding phthalic anhydride to a 40% solution of amine in toluene in a 1/1 mole ratio at 80° C. The product was recovered by vacuum drying at 50° C., 0.05 mmHg for 20.5 hours. Phthalic anhydride sublimation was observed. This method makes no mention of the presence of any ammonium salt in the resultant product.

U.S. Pat. No. 4,402,708 describes a method for preparing N,N-dioctadecyl phthalamic acid dioctadecyl ammonium salt and N,N-diarachidyl phthalamic acid diarachidyl ammonium salt. Phthalic anhydride was added to a 10% solution of amine in toluene in an anhydride to amine mole ratio of 1/2. The product was recovered by filtering and film evaporating a 1/1 toluene/n-heptane solution at 55° C., 40 mmHg.

Phthalamic acids have also been prepared by melting phthalic anhydride at 131° C. and subsequent addition of molten secondary amine. The reactants to be added in an equimolar ratio. At the temperature used in this method, 131° C, excessive phthalic anhydride sublimation occurs and increased product degradation is observed. This method makes no mention of the presence of any ammonium salt in the resultant product.

Phthalamic acids have been prepared by addition of a solution of secondary amine in isopropanol at 78° C. to a phthalic anhydride/isopropanol slurry at 78° C. in a one to one phthalic anhydride/amine molar ratio with subsequent vacuum stripping of the solvent. This method utilizes isopropanol as the solvent for the reaction. Isopropanol, a secondary amine, reacts with phthalic anhydride to yield isopropyl mono ester of phthalic acid. At 78° C., as much as 40% of the product may be this ester.

Each of these methods produces a mixture of the desired phthalamic acid and an ammonium phthalamate salt. However, these methods make no mention of the presence of any ammonium salt in the resultant product.

SUMMARY OF THE INVENTION

The present invention provides surfactant solutions comprising an effective amount of a salt of the following general:

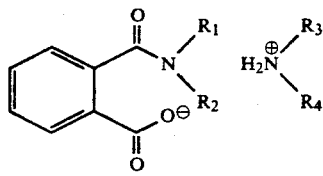

wherein $R_1$, $R_2$, $R_3$, and $R_4$ are the same or different and represent straight or branched chain alkyl groups having 10 to 40 carbon atoms, or aryl straight or branched chain alkyl groups having 10 to 40 carbon atoms.

The present invention also provides surfactant solutions comprising an effective surfactant amount of an acid of the following general formula:

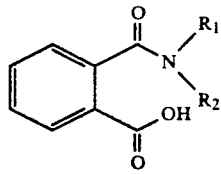

wherein $R_1$ and $R_2$ are the same or different and represent straight or branched chain alkyl groups having 10 to 40 carbon atoms, or aryl straight or branched chain alkyl groups having 10 to 40 carbon atoms.

The present invention also provides surfactant solutions comprising an effective surfactant amount of a mixture of a salt of formula I above and an acid of formula II.

In addition, the present invention provides formulated conditioning shampoos comprising an effective conditioning amount of a salt of formula I. The invention further provides a formulated conditioning shampoo comprising an effective conditioning amount of a mixture of a salt of formula I above and an acid salt of formula II above.

The present invention also provides emulsifier solutions comprising an effective emulsifier amount of a salt of formula I above. The present invention also provides emulsifier solutions comprising an effective emulsifier amount of a mixture of a salt of formula I above and an acid of formula II above.

DETAILED DESCRIPTION OF THE INVENTION

It has been discovered that when a certain phthalamic acid and phthalamic acid ammonium salts or mixtures thereof are incorporated into a typical shampoo base with a non-volatile, insoluble silicone and the resulting formulated shampoo product is evaluated in a laboratory setting on hair swatches or in a salon setting on human subjects (Table 4A), perceptual improvements in detangling, wet combability, dry combability, and static control are readily observed. These compounds unexpectedly function as emulsifying/suspending agents for silicones, as anti-static or conditioning agents, and as surfactants. In CTFA (Cosmetics, Toiletry, and Fragrance Association) nomenclature, phthalamic acids may be designated as amido carboxy benzoic acids, and phthalamic acid ammonium salts may be designated ammonium amido carboxy benzoates.

The laboratory and salon results indicate that certain phthalamic acid ammonium salts, acids and/or mixtures thereof, may have a dual function in this type of application. The shampoo formulations prepared according to the present invention with certain phthalamic acid, phthalamic acid ammonium salts or mixtures thereof, exhibit excellent flow properties and have long term stability at different storage temperatures. The finished formulations retain all of the above properties after at least three freeze-thaw cycles (Table 4B) and are easily preserved using common preservatives.

Accordingly, the present invention encompasses formulated conditioning shampoos comprising salts of formula I

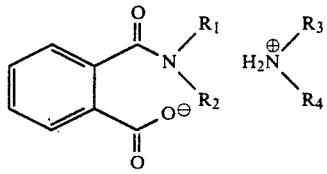

wherein $R_1$, $R_2$, $R_3$, and $R_4$ are the same or different and represent straight or branched chain alkyl groups having 10 to 40 carbon atoms, or aryl straight or branched chain alkyl groups having 10 to 40 carbon atoms.

The present invention also encompasses formulated conditioning shampoos comprising mixtures of a salt of formula I above and an acid of formula II

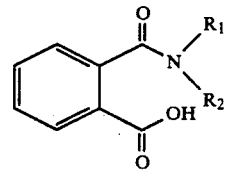

wherein $R_1$ and $R_2$ are the same or different and represent straight or branched chain alkyl groups having 10 to 40 carbon atoms, or aryl straight or branched chain alkyl groups having 10 to 40 carbon atoms.

In a preferred embodiment of the formulated conditioning shampoo of the present invention, $R_1$, $R_2$, $R_3$, and R4 are derived from hydrogenated tallow. Because tallow is a mixture of C-14 to C18 fatty acids, and amines derived from tallow are hence a mixture of tallow amines, the phthalamic acids and/or the ammonium salts thereof used in the present invention may therefore have R groups that are the same or different.

In a particularly preferred embodiment of the formulated conditioning shampoo of the present invention, the shampoo comprises N,N-di(hydrogenated tallow) phthalamic acid di(hydrogenated tallow) ammonium salt. In another particularly preferred embodiment of the present invention, the shampoo comprises a mixture of N,N-di(hydrogenated tallow) phthalamic acid and N,N-di(hydrogenated tallow) phthalamic acid di(hydrogenated tallow) ammonium salt.

The effective concentration of these phthalamic acid ammonium salts and mixtures of the phthalamic acids and phthalamic acid ammonium salts in the formulated conditioning shampoos of the present invention varies from about 0.05% to about 20% on an active basis. A presently preferred use concentration appears to be between about 0.5% to 10%. Various formulated shampoos are shown in Tables 1, 2 and 3.

The formulated conditioning shampoos of the present invention comprising a mixture of a salt of formula I and an acid of formula II have ratios of acid to salt varying from about 90:10 to about 10:90. Preferred ratios of acid to salt vary from about 70:30 to about 30:70.

Furthermore, it has been found that the conditioning properties of the shampoos of the present invention are obtained when the pH of the shampoo mixture is adjusted to between about 3.0 and about 9.0. A more preferred range of pH in the formulated shampoos is from about 4.5 to 6.5.

As can be seen from the results shown in Table 4A, the shampoo formulations of the invention demonstrated superior overall conditioning attributes, both in a conditioning and conditioning/anti-dandruff formulation. Further, as shown by results in Table 4B, the inventive shampoo formulations readily passed freeze/thaw and stability studies over a pH range of 3.0 to 9.0, whereas similar formulations without the di(hydrogenated tallow) phthalamic acid/ammonium salts of the invention failed.

The formulated conditioning shampoos of the present invention are readily manufactured using a conventional single-phase, hot process. The manufacture of the conditioning shampoos using a single-phase, hot process is simple and, therefore, preferred over multi-phase processes.

The formulated conditioning shampoos of the present invention are prepared by incorporating salts of formula I or a mixture of salts of formula I and acids of formula II in a typical shampoo base such as those shown in Tables 1, 2, and 3.

Certain mixtures of phthalamic acids and phthalamic acid ammonium salts are also excellent emulsifiers/suspending agents for non-volatile and volatile silicones and other water insoluble emollient oils. The utilization of this technology can be naturally extended to car wax formulations, textile lubricants, textile anti-static agents, shoe polishes, antiperspirants, hair conditioners (leave-on or rinse out type) and to other uses of silicone products.

Further, the invention also provides surfactant solutions comprising an effective surfactant amount of salts of formula I

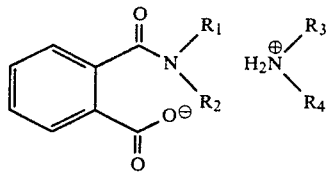

wherein
$R_1$, $R_2$, $R_3$, and $R_4$ are the same or different and represent straight or branched chain alkyl groups having 10 to 40 carbon atoms, or aryl straight or branched chain alkyl groups having 10 to 40 carbon atoms.

This invention further provides surfactant solutions comprising an effective amount of a mixture of a salt of formula I above and an acid of formula II

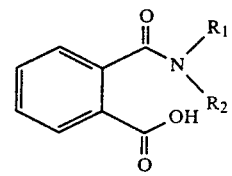

wherein
$R_1$ and $R_2$ are the same or different and represent straight or branched chain alkyl groups having 10 to 40 carbon atoms, or aryl straight or branched chain alkyl groups having 10 to 40 carbon atoms.

The surfactant solutions of the present invention may be used as surfactants per se, as caustic-stabile surfactants, as chlorine-stabile surfactants, as cosmetic emulsifiers for personal care products, such as skin creams, skin lotions, hair conditioners, etc., as fast-breaking skin-care product emulsifiers; as emulsifiers for liquid hand, facial and body soaps and bar soaps; as emulsifiers for agricultural chemicals, as domestic fabric softeners; as destructible latex polymerization surfactants in coating and/or adhesive systems, as domestic detergent additives, such as in heavy-duty detergents, in light-duty detergents, in dishwashing detergents, in various hard-surface cleaners, etc., as emulsifiers for portland cement and concrete; as flotation/benefication additives for various mineral ores; as additives for electroplating and/or surface finishing baths for metal goods; as additives for plaster, gypsum and miscellaneous building materials; as enhanced oil recovery additives; as wetting, lubricating, and penetrating surfactants for textile processing; as pulp digestive additives; as surfactants for polyurethane/isocynaurate foam systems; as pour-point depressants for transporting viscous petroleum oils; as industrial surfactants for emulsifying a wide variety of oily materials or oliginous materials such as linseed oils, alkyd resins, polybutylenes, silicones. polysilicones, silicone gums, etc.; as low temperature stabilizers for fatty alcohol/water emulsions; as suspending agents for various particulate material, such as coal tar, sulfur or coal; etc.

Related surfactants and surfactant compositions are disclosed in Goze et al., U.S. patent application No. 07/391,187 filed Aug. 8, 1989, and assigned to the same assignee as the instant application. This disclosure is hereby incorporated by reference.

The present invention also provides surfactant solutions comprising a mixture of a salt of formula I and an acid of formula II having ratios of acid to salt ranging from about 90:10 to about 10:90. Preferred ratios of acid to salt range from about 70:30 to about 30:70. The invention also provides surfactant solutions comprising the acid or salt per se.

It has also been unexpectedly found that phthalamic acid ammonium salts function as superior emulsifiers or suspending agents for active agents in anti-dandruff shampoos, such as zinc pyrithione (ZPT) in typical anti-dandruff shampoos. An example of anti-dandruff shampoo with typical phthalamic acid ammonium salt of interest is shown in Table 2 below. Similarly, anti-dandruff shampoo compositions can be formulated with other anti-dandruff agents, such as selenium sulfide, colloidal or powdered sulfur, coal tar mixtures, etc. Certain phthalamic acid ammonium salts of interest also function as emulsifiers and suspending agents in conditioning/anti-dandruff shampoo compositions.

An example of a conditioning/anti-dandruff shampoo composition with phthalamic acid ammonium salts is shown in Table 3 below. Compositions of this type have been found to provide excellent detangling, wet combability, dry combability, and static control characteristics on hair swatches in a laboratory setting and on human subjects with different hair profiles in a beauty salon setting. These compositions also exhibited excellent long-term stability at various storage temperatures, including three freeze-thaw cycles. The effective concentration of phthalamic acid ammonium salts as a suspending agent varies from about 0.05% to about 20.0% on an active basis. A presently preferred use concentration appears to be between about 0.5% to 0% on an active basis.

Yet further, the invention also provides emulsifier solutions comprising an effective emulsifier amount of salts of formula I

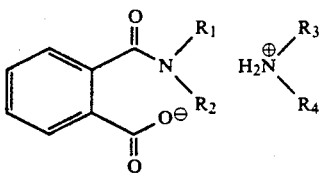

wherein $R_1$, $R_2$, $R_3$, and $R_4$ are the same or different and represent straight or branched chain alkyl groups having 10 to 40 carbon atoms, or aryl straight or branched chain alkyl groups having 10 to 40 carbon atoms.

This invention further provides emulsifier solutions comprising an effective emulsifier amount of a mixture of a salt of formula I above and an acid of formula II

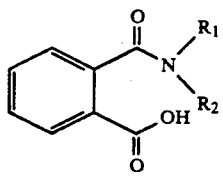

wherein $R_1$ and $R_2$ are the same or different and represent straight or branched chain alkyl groups having 10 to 40 carbon atoms, or aryl straight or branched chain alkyl groups having 10 to 40 carbon atoms.

TABLE 1

CONDITIONING SHAMPOO

| Ingredient | Formulation 1 wt. % (active) | Formulation 2 wt. % (active) |
|---|---|---|
| 1. Deionized Water | Q.S. to 100.00 | Q.S. to 100.00 |
| 2. Tetrasodium EDTA | 0.20 | 0.20 |
| 3. STEPANOL ® AM-V[1] | 20.00 | 20.00 |
| 4. NINOL ® 40 CO[2] | 2.00 | 2.00 |
| 5. N,N-di(hydrogenated tallow) Phthalamic acid/ammonium salt at a ratio of 80:20 | — | 5.00 |
| 6. Silicone DC 200 (12,500 cps) (a dimethicone) | 0.50 | 0.50 |
| 7. Citric Acid 50% | Q.S. | Q.S. |
| 8. Sodium Hydroxide 50% | Q.S. | Q.S. |
| 9. 1,3,5,5-tetramethyl hydantoin | 0.20 | 0.20 |
| 10. Ammonium Chloride | 0.20 | 0.20 |

[1]Registered trademark of Stepan Co. for ammonium lauryl sulfate
[2]Registered trademark of Stepan Co. for cocomide diethanolamine

TABLE 2

ANTI-DANDRUFF SHAMPOO

| Ingredient | Formulation 3 wt. % (active) | Formulation 4 wt. % (active) |
|---|---|---|
| 1. Deionized Water | Q.S. to 100.00 | Q.S. to 100.00 |
| 2. Tetrasodium EDTA | 0.20 | 0.20 |
| 3. STEPANOL ® AM-V[1] | 20.00 | 20.00 |
| 4. NINOL ® 40 CO[2] | 2.00 | 2.00 |
| 5. N,N-di(hydrogenated tallow) Phthalamic acid/ammonium salt at a ratio of 30:70 | — | 5.00 |
| 6. Zinc Pyrithione 48% Dispersion | 4.20 | 4.20 |
| 7. Citric Acid 50% | Q.S. | Q.S. |
| 8. Sodium Hydroxide 50% | Q.S. | Q.S. |
| 9. 1,3,5,5-tetramethyl hydantoin | 0.20 | 0.20 |
| 10. Ammonium Chloride | 0.20 | 0.20 |

[1]Registered trademark of Stepan Co. for ammonium lauryl sulfate
[2]Registered trademark of Stepan Co. for cocomide diethanolamine

TABLE 3

CONDITIONING/ANTI-DANDRUFF SHAMPOO

| Ingredient | Formulation 5 wt. % (active) | Formulation 6 wt. % (active) |
|---|---|---|
| 1. Deionized Water | Q.S. to 100.00 | Q.S. to 100.00 |
| 2. Tetrasodium EDTA | 0.20 | 0.20 |
| 3. STEPANOL ® AM-V[1] | 20.00 | 20.00 |
| 4. NINOL ® 40 CO[2] | 2.00 | 2.00 |
| 5. N,N-di(hydrogenated Tallow) phthalamic acid/ammonium salt at a ratio of 50:50 | — | 5.00 |
| 6. Silicone DC 200 (12,500 cps) (a dimethicone) | 0.50 | 0.50 |
| 7. Zinc Pyrithione 48% Dispersion | 4.20 | 4.20 |
| 8. Citric Acid 50% | Q.S. | Q.S. |
| 9. Sodium Hydroxide 50% | Q.S. | Q.S. |
| 10. 1,3,5,5-tetramethyl hydantoin | 0.20 | 0.20 |
| 11. Ammonium Chloride | 0.20 | 0.20 |

[1]Registered trademark of Stepan Co. for ammonium lauryl sulfate
[2]Registered trademark of Stepan Co. for cocomide diethanolamine

TABLE 4A

COMPARATIVE PERFORMANCE EVALUATION - CONDITIONING SHAMPOO AND CONDITIONING/ANTI-DANDRUFF SHAMPOO

| CONDITIONING* ATTRIBUTES | CONDITIONING SHAMPOO | CONDITIONING/ ANTI-DANDRUFF SHAMPOO |
|---|---|---|
| Detangling | Form. 2 > Form. 1 > Baseline control | Form. 6 > Form. 5 > Baseline control |
| Wet Combing | Form. 2 > Form. 1 > Baseline control | Form. 6 > Form. 5 > Baseline control |
| Dry Combing | Form. 2 > Form. 1 > Baseline control | Form. 6 > Form. 5 > Baseline control |
| Static Control/ Flyaway | Form. 2 > Form. 1 = Baseline control | Form. 6 > Form. 5 = Baseline control |

Baseline control Formulation is substantially the same as formulations 1 and/or 5 without silicone DC 200 (12,500 cps)
*A controlled half-head salon evaluation by an experienced licensed beautician on a panel of 30 subjects was used as a method for determining the listed attributes above.

TABLE 4B

COMPARATIVE STABILITY EVALUATION

| Formula # | Temp. (°F.) over 1 Month Period | | | | pH over 1 Month Period | | |
|---|---|---|---|---|---|---|---|
| | −32° | +35° | Ambient | 110° | 3.0 | 7.0 | 9.0 |
| Baseline Control | P | S | S | S | S | S | S |
| Formula 1 | U | U | U | U | U | U | U |
| 2 | P | S | S | S | S | S | S |
| 3 | U | U | U | U | U | U | U |
| 4 | P | S | S | S | S | S | S |
| 5 | U | U | U | U | U | U | U |
| 6 | P | S | S | S | S | S | S |

P = Pass (3) Freeze/Thaw cycles
S = Stable
U = Unstable

The present invention also encompasses methods for preparing mixtures of phthalamic acids and their corresponding ammonium salts.

The invention is illustrated further by the following examples which are not to be construed as limiting the invention in scope or spirit to the specific procedures described in them.

EXAMPLE 1

Preparation of a mixture of N,N-di(hydrogenated tallow) phthalamic acid and N,N-di(hydrogenated tallow) phthalamic acid di-(hydrogenated tallow) ammonium salt One mole (148.0 g) of flaked phthalic anhydride (PA) was charged into a 4-neck 5-liter round bottomed flask reactor equipped with a mechanical stirrer, a thermocouple temperature controller and a heating mantle. A charge of 650 g of isopropyl alcohol (USP grade) was added to the reactor to achieve a slurry of about 50% solids. One mole (about 502 g) of molten di(hydrogenated tallow) amine was slowly added to the slurry in the reactor with continuous stirring. The temperature of the reaction mass was allowed to stabilize at about 45°–55° C. with gradual addition of the amine and cooling of the reactor flask. Amine addition was completed in about 0.5 to 1 hours. Thereafter the reactor was maintained at about 60° C. until the PA flakes dissipated and IR spectroscopic analysis showed no detectable amounts of PA in the reaction mass. Isopropyl alcohol was then removed under vacuum (about 1–50 mmHg) On analysis, about 62 mole % acid and about 38 mole % salt were found with an average molecular weight of about 782.

EXAMPLE 2

Preparation of a Conditioning Shampoo

Water was first added into a suitable vessel equipped with agitation, heating and cooling capabilities. While the water was agitated and heated slowly, tetrasodium EDTA, STEPANOL ® AM-V (ammonium lauryl sulfate) and NINOL ® 40 CO (cocomide diethamolamine) were added. At about 145° F. a 70:30 mixture of N,N-di(hydrogenated tallow) phthalamic acid and N,N-di(hydrogenated tallow) phthalamic acid N,N-di(hydrogenated tallow) ammonium salt, followed by silicone DC 200 were added to the mixture. The mixture was heated to 160°–165° F. and emulsified for 20–30 minutes at high speed while maintaining the temperature between 160°–165° F. The mixture was slowly cooled with agitation set at medium speed. When the temperature of the mixture cooled to about 110° C., 1,3,5,5-tetramethyl hydantoin and ammonium chloride were added. The pH was checked and adjusted as necessary with ammonium hydroxide or citric acid to a value between about 4.5 to 6.5. The viscosity was checked and adjusted as necessary with ammonium chloride to a value between 4000 and 6000 cps.

EXAMPLE 3

Preparation of an anti-dandruff shampoo

Water was first added into a suitable vessel equipped with agitation, heating and cooling capabilities. While the water was agitated and heated slowly, tetrasodium EDTA, STEPANOL ® AM-V, (ammonium lauryl sulfate) and NINOL ® 40 CO, (cocomide diethanolamine) were added. At about 145° F., a 70:30 mixture of N,N-di(hydrogenated tallow) phthalamic acid and N,N-di(hydrogenated tallow) phthalamic acid N,N-di(hydrogenated tallow) ammonium salt, followed by silicone DC 200 and ZPT (zinc pyrithione. 48% dispersion), were added to the mixture. The mixture was heated to 160°–165° F. and emulsified for 20–30 minutes at high speed while maintaining the temperature between 160°–165° F. The mixture was slowly cooled with agitation set at medium speed. When the temperature of the mixture cooled to about 110° C., 1,3,5,5-tetramethyl hydantoin and ammonium chloride were added. The pH was checked and adjusted as necessary with ammonium hydroxide or citric acid to a value between about 4.5 and 6.5. The viscosity was checked and adjusted as necessary with ammonium chloride to a value between 4000 and 6000 cps.

EXAMPLE 4

Preparation of an Anti-dandruff/Conditioning Shampoo

Water was first added into a suitable vessel equipped with agitation, heating and cooling capabilities. While the water was agitated and heated slowly, tetrasodium EDTA, STEPANOL ® AM-V, (ammonium lauryl sulfate), and NINOL ® 40 CO (cocomide diethanolamine) were added. At about 145° F., a 70:30 mixture of N,N-di(hydrogenated tallow) phthalamic acid and N,N-di(hydrogenated tallow) phthalamic acid N,N-di(hydrogenated tallow) ammonium salt, followed by silicone DC 200 and ZPT (zinc pyrithione, 48% dispersion) were added to the mixture. The mixture was heated to 160°–165° F. and emulsified for 20–30 minutes at high speed while maintaining the temperature between 160°–165° F. The mixture was slowly cooled with agitation set at medium speed. When the temperature of the mixture cooled to about 110° C., 1,3,5,5-tetramethyl hydantoin and ammonium chloride were added. The pH was checked and adjusted as necessary with ammonium hydroxide or citric acid to a value between about 4.5 and 6.5. The viscosity was checked and adjusted as necessary with ammonium chloride to a value between 4000 and 6000 cps. As will be appreciated, the above formulations provide exemplary surfactants and cocomides only, and other primary surfactants, amides and mixtures thereof may be used.

From the foregoing it will be appreciated that, although specific embodiments of the invention have been described herein for purposes of illustration, various modifications may be made without deviating from the spirit and scope of the invention.

What is claimed is:

1. In a formulated shampoo comprising at least one surfactant and a second member selected from the group consisting of a silicone compound conditioning agent, an anti-dandruff agent and mixtures thereof, the improvement comprising an amount in the range of about 0.05% to about 20% of a salt of the formula:

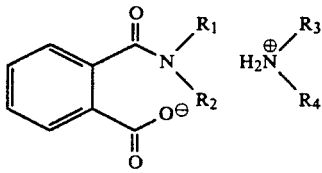

wherein
$R_1$, $R_2$, $R_3$ and $R_4$ are the same or different and represent straight or branched chain alkyl groups having 10 to 40 carbon atoms, or aryl straight or branched chain alkyl groups having 10 to 40 carbon atoms.

2. A formulated shampoo according to claim 1 wherein the amount of said salt in the shampoo is about 0.50 to about 10%.

3. A formulated shampoo according to claim 2, wherein said shampoo has a pH value ranging from 3.0 to about 9.0.

4. A formulated shampoo according to claim 3, wherein said shampoo has a pH value ranging from about 4.5 to about 6.5.

5. A formulated shampoo according to claim 1, wherein $R_1$, $R_2$, $R_3$ and $R_4$ are hydrogenated tallow fatty alkyl groups.

6. A formulated shampoo according to claim 1, wherein said salt is N,N-di(hydrogenated tallow) phthalamic acid N,N di-(hydrogenated tallow) ammonium salt.

7. In a formulated shampoo, the improvement comprising an amount in the range of about 0.05% to about 20% of a mixture of an acid of the formula:

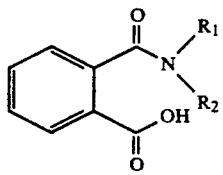

wherein
$R_1$ and $R_2$ are the same as different and represent straight or branched chain alkyl groups having 10 to 40 carbon atoms, or aryl straight or branched chain alkyl groups having 10 to 40 carbon atoms, and a salt of the formula:

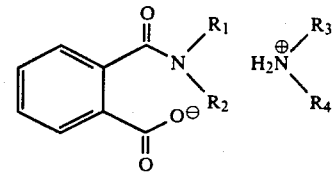

wherein
$R_1$, $R_2$, $R_3$, and $R_4$ are the same or different and represent straight or branched chain alkyl groups having 10 to 40 carbon atoms, or aryl straight or branched chain alkyl groups having 10 to 40 carbon atoms.

8. A formulated shampoo according to claim 7, wherein the amount of said mixture of the acid and salt in the shampoo is about 0.05% to about 10%.

9. A formulated shampoo according to claim 8, wherein said shampoo has a pH value ranging from about 3.0 to about 9.0.

10. A formulated shampoo according to claim 9, wherein said shampoo has a pH value ranging from about 4.5 to about 6.5.

11. A formulated shampoo according to claim 7, wherein $R_1$, $R_2$ $R_3$ and $R_4$ are hydrogenated tallow fatty alkyl groups.

12. A formulated shampoo according to claim 7, wherein the acid and salt are present in said mixture in a ratio ranging from about 90:10 to about 10:90.

13. A formulated shampoo according to claim 7, wherein the acid and salt are present in said mixture in a ratio ranging from about 70:30 to about 30:70.

14. In a formulated shampoo according to claim 7 including at least one conditioning agent.

15. In a formulated shampoo according to claim 14 wherein the conditioning agent is selected from the group consisting of at least one silicone compound or at least one quaternary ammonium compound and mixtures thereof.

16. In a formulated shampoo according to claim 7 including at least one anti-dandruff agent.

17. In a formulated shampoo according to claim 16 wherein the anti-dandruff agent is selected from the groups consisting of zinc pyrithione, selenium sulfide, colloidal or powder sulfur, coal tar derivatives and mixtures thereof.

18. In a formulated shampoo according to claim 7 including at least one conditioning agent and at least one anti-dandruff agent.

19. In a formulated shampoo according to claim 18 wherein the conditioning agent is selected from the group consisting of at least one silicone compound or at least one quaternary ammonium compound and mixture thereof and wherein the anti-dandruff agent is selected from the groups consisting of zinc pyrithione, selenium sulfide, collodial or powder sulfur, coal tar derivatives and mixtures thereof.

20. In a formulated shampoo, the improvement comprising an amount in the range of about 0.5% to about 20% of a mixture of N,N-di(hydrogenated tallow) phthalamic acid and N,N-di(hydrogenated tallow) phathalamic acid, N,N-di(hydrogenated tallow) phthalamic ammonium salt.

21. In a formulated shampoo according to claim 1 including at least one conditioning agent.

22. In a formulated shampoo according to claim 21 wherein the conditioning agent is selected from the group consisting of at least one silicone compound and at least one quaternary ammonium compound and mixtures thereof.

23. In a formulated shampoo according to claim 1 including at least one anti-dandruff agent.

24. In a formulated shampoo according to claim 23 wherein the anti-dandruff agent is selected from the groups consisting of zinc pyrithione, selenium sulfide, collodiol sulfur, coal tar derivatives and mixtures thereof.

25. In a formulated shampoo according to claim 1 including at least one conditioning agent and at least one anti-dandruff agent.

26. In a formulated shampoo according to claim 25 wherein the conditioning agent is selected from the group consisting of at least one silicone compound and at least one quaternary ammonium compound and mixtures thereof and wherein the anti-dandruff agent is selected from the groups consisting of zinc pyrithione, selenium sulfide, collodial or powder sulfur, coal tar derivatives and mixtures thereof.

27. In a formulated shampoo comprising at least one surfactant and a second member selected from the group consisting of a silicone compound conditioning agent, an anti-dandruff agent and mixtures thereof the improvement comprising an amount in the range of about 0.5% to about 20% of N,N-di(hydrogenated tallow) phathalamic acid N,N-di(hydrogenated tallow) ammonium salt.

* * * * *

UNITED STATES PATENT AND TRADEMARK OFFICE
CERTIFICATE OF CORRECTION

PATENT NO. : 5,015,415
DATED : May 14, 1991
INVENTOR(S) : Jean N. Goze et al

It is certified that error appears in the above-indentified patent and that said Letters Patent is hereby corrected as shown below:

At. col. 2, line 61, insert the following formula after "ammonium salts of the formula:"

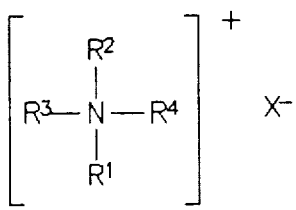

At col. 3, line 3, insert the following formula after "formula:"

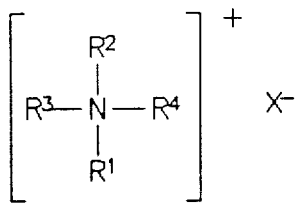

At col. 9, line 32, change "0.5% to 0%" to -- 0.5% to 10% --.

Signed and Sealed this

First Day of February, 1994

Attest:

BRUCE LEHMAN

*Attesting Officer*    *Commissioner of Patents and Trademarks*